United States Patent [19]

Gale et al.

[11] 4,206,226

[45] Jun. 3, 1980

[54] USE OF 4-CARBOXY-PHTHALATO-(1,2-DIAMINOCYCLOHEXANE)-PLATINUM(II) AND ALKALI METAL SALTS THEREOF IN ALLEVIATING L1210 MURINE LEUKEMIA

[75] Inventors: Glen R. Gale; Paul Schwartz, both of Charleston, S.C.

[73] Assignee: The United States of America as represented by the Department of Health, Education and Welfare, Washington, D.C.

[21] Appl. No.: 926,035

[22] Filed: Jul. 19, 1978

Related U.S. Application Data

[63] Continuation-in-part of Ser. No. 828,926, Aug. 26, 1977.

[51] Int. Cl.² ............................................. A61K 31/28
[52] U.S. Cl. ..................................................... 424/287
[58] Field of Search ........................................ 424/287

*Primary Examiner*—Jerome D. Goldberg
*Attorney, Agent, or Firm*—John S. Roberts, Jr.

[57] ABSTRACT

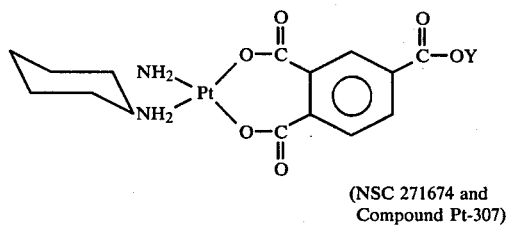

(NSC 271674 and Compound Pt-307)

Y=H, alk met

4-Carboxyphthalato(1,2-diaminocyclohexane) platinum(II) (and alkali metal salts thereof) has shown anti-leukemic activity in mice against murine leukemia L1210. It is effective in dosages of 5–60 mg/kg of body weight and is potentiated in a treatment with cyclophosphamide (CY) (50 mg/kg of body weight) to which may be added 5-fluorouracil (5-FU) (75 mg/kg of body weight) or hydroxyurea (HU) (1000 mg/kg of body weight). Some previous platinum chelate compounds show dosage limitation due to renal impairment but the free carboxyl of the present Pt compound offers a possible route of oral administration and absorption by the stomach.

The Pt compound may be prepared by reacting the known dichloro(1,2-diaminocyclohexane) platinum(II) (NSC 194814) with silver nitrate to replace chloro with nitro. Subsequently, benzene tricarboxylic acid is added to form an off-white precipitate (2 hrs, dark, 5° C.) of the desired product which is preferably utilized as the alkali metal salt.

The 4-carboxyphthalato(1,2-diaminocyclohexane)-platinum(II) and alkali metal salts thereof may be combined in multiple drug regimen with substantially improved yield cures over the parent compound. For example, the compound denoted Pt-307 may be combined in a dual regimen with cyclophosphamide (CY) and in a triple drug regimen of Pt-307 plus cyclophosphamide (CY) and either 5-fluorouracil (5-FU) or hydroxyurea (HU) as the third component.

Additionally, the present compound (NSC 271674) has shown superior results in testing for renal toxicity against the parent compound (NSC 119875, cis-dichlorodiamino platinum II) and further the present compound appears to be active against strains of murine leukemia wherein the same NSC 119875 has exhausted its activity.

4 Claims, No Drawings

USE OF 4-CARBOXY-PHTHALATO-(1,2-DIAMINOCYCLOHEXANE)-PLATINUM(II) AND ALKALI METAL SALTS THEREOF IN ALLEVIATING L1210 MURINE LEUKEMIA

This application is a continuation-in-part application of U.S. Ser. No. 828,926 filed Aug. 29, 1977.

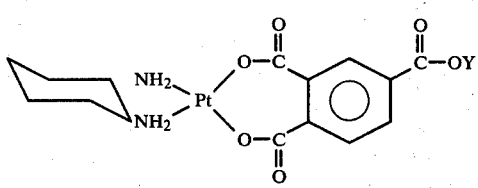

(NSC 271674 and Compound Pt-307)

Y=H, alk met

[4-Carboxyphthalato(1,2-diaminocyclohexane)-platinum(II) and alkali metal salts thereof]

4-Carboxyphthalato(1,2-diaminocyclohexane)-platinum(II) (and alkali metal salts thereof) has shown antileukemic activity in mice against murine leukemia L1210. It is effective in dosages of 5–60 mg/kg of body weight and is potentiated in a treatment with cyclophosphamide (CY) (50 mg/kg of body weight) to which may be added 5-fluorouracil (5-FU) (75 mg/kg of body weight) or hydroxyurea (HU) (1000 mg/kg of body weight). Some previous platinum chelate compounds show dosage limitation due to renal impairment but the free carboxyl of the present composition offers a possible route of oral injection and absorption by the stomach.

The compound may be prepared by reacting the known dichloro(1,2-diaminocyclohexane)platinum(II) (NSC 194814) with silver nitrate to replace chloro with nitro. Subsequently, benzene tricarboxylic acid is added to form an off-white precipitate (2 hrs, dark, 5° C.) of the desired product which is preferably utilized as the alkali metal salt.

The 4-carboxyphthalato(1,2-diaminocyclohexane)-platinum(II) and alkali metal salts thereof may be combined in multiple drug regimen with substantially improved yield cures over the parent compound. For example, the compound denoted Pt-307 may be combined in a dual regimen with cyclophosphamide (CY) and in a triple drug regimen of Pt-307 plus cyclophosphamide (CY) and either 5-fluorouracil (5-FU) or hydroxyurea (HU) as the third component.

It is understood in this specification and claims that where the compound 4-carboxyphthalato(1,2-diaminocyclohexane)platinum(II) is utilized it is designed and meant to apply to the free acid as well as alkali metal salts thereof such as sodium, potassium, lithium, etc.

PRIOR ART

The following patents provide background material to the present invention.

U.S. Pat. No. 3,892,790 Tobe et al—The compounds disclosed are platinum(II) halogeno complexes such as cis-dichloroPt(II) where the remaining bonds are bis(cyclopropylamine), bit(cyclobutylamine), bis(cyclopentylamine), bis(cyclohexylamine) and bis(cycloheptylamine).

U.S. Pat. No. 3,904,663 Tobe et al—Formula 2 in the list of compounds bridging columns 1 and 2 is cyclohexane (trans)-1,2-diamine platinum(II) and the compounds for claim purposes are illustrated by dichloro(orthophenylene-diamine)platinum(II).

The following literature references are deemed of interest:

J. M. Hill et al, "Platinum Coordination Compounds in the Treatment of Acute Leukemia and Other Malignant Diseases with Particular Reference to Malonato 1,2-Diaminocyclohexane Platinum(II)," *Journal of Clinical Hematology and Oncology*, 7:681–697 (1977). This compound abbreviated PHM has a structure disclosed as follows:

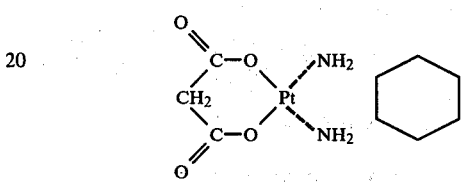

Paul Schwartz et al, "Preparation and Antitumor Evaluation of Water-Soluble Derivatives of Dichloro(1,2-Diaminocyclohexane)Platinum(II) (NSC-194814)," *Cancer Treatment Reports*, 61:1519–1525 (1977).

Glen R. Gale et al, "Potentiating Action of 5-Fluorouracil When Used in Combination with Platinum Compounds and Cyclophosphamide in Treatment of Advanced L1210 Leukemia," accepted for publication in *Bioinorganic Chemistry*.

Glen R. Gale et al, "Synergistic Action of High-Dose Hydroxyurea When Used With Cyclophosphamide and Certain New Organoplatinum Complexes in Treatment of Advanced L1210 Leukemia," accepted for publication in *Cancer*.

The utilization of the present compound, 4-carboxyphthalato(1,2-diaminocyclohexane)platinum(II), against L1210 murine leukemia is not anticipated by the effective prior art and it is noted that the last three literature references, one to Schwartz et al and two to Gale et al (as yet unpublished) are useful in the preparation of the present specification of invention.

The recent chemotherapy of utilizing platinum coordination compounds dates back to some work by Rosenberg and co-workers as reported in *Nature*, 205:698–699 (1965) and also in *Nature*, 222:385–386 (1969). It was early found that the cis platinous compounds had superior activity and as a starting point was mentioned cis-dichloro(1,2-diaminocyclohexane)-platinum(II) known as DDCP and cis-platinous diaminodichloride (PDD). In general, newer antitumor agents modified or replaced the chlorides in dichloro-1,2-diaminocyclohexane platinum(II) (NSC 194814) by organic or inorganic anion. One difficulty with the diaminocyclohexane complex is its low solubility. It was known that the diaminocyclohexane moiety reduces the toxicity while increasing the antitumor activity of complexes with highly reactive ligands as, for example, nitrato or sulfato groups.

In the present application a dicarboxylic acid dianion (the phthalate) relates to the central platinum(II) cation and forms neutral complexes.

Additionally, while phthalato(1,2-diaminocyclohexane)platinum(II) (NSC 268255) is very insoluble, the 4-carboxyphthalato(1,2-diaminocyclohexane)platinum-(II) (NSC 271674) readily dissolves in 1% sodium bicarbonate solution via formation of the sodium carboxylate.

PREPARATION OF COMPOUND 4-CARBOXYPHTHALATO-(1,2-DIAMINOCYCLOHEXANE)PLATINUM(II)

4-Carboxyphthalato(1,2-diaminocyclohexane)-platinum(II) has the following structure:

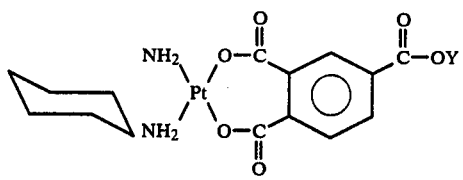

Y=H, alk met
Molecular formula: $C_{15}H_{18}N_2O_6Pt$
Molecular weight: 517.44

This compound may be prepared by the following synthetic route:

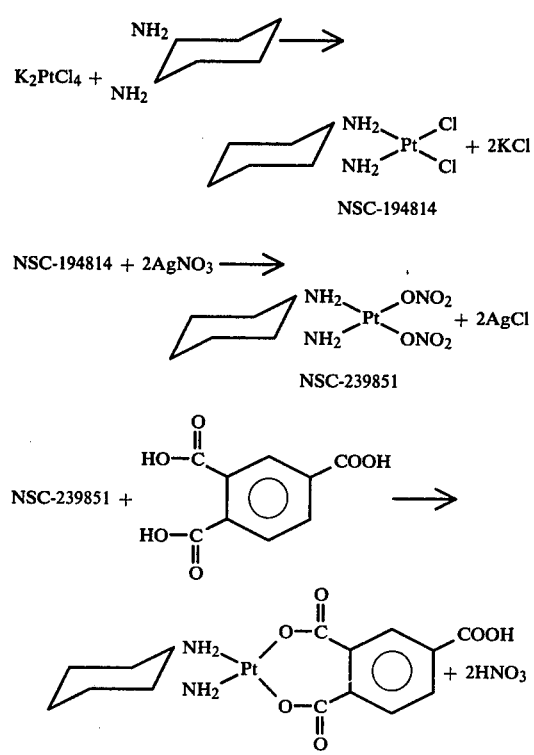

A specific preparation is set out post as Example 1.

DOSAGE

Compound Pt-307 was administered usually in a dosage regimen of 5-60 mg/kg of body weight. This was given as a single dose or on Days 1, 5, and 9 in the standard National Institutes of Health 10-day testing. In this testing Pt-307 was the same compound as NSC 271674. In general, the ternary combination such as Pt+CY+FU enhanced markedly the increased lifespan of treated mice. Collectively the cure rate (greater than 60-day survival) was less than 6% with the Pt+CY combinations and was increased to over 63% upon inclusion of FU in the regimen. This particular combination was somewhat superior to that obtained with hydroxyurea (HU) below where HU was used as a third drug with the Pt+CY combination.

It is noted that 5-fluorouracil (5-FU) has also been shown to potentiate the action of irradiation. For example, mean survival times were significantly increased in patients who received combined FU and radiation treatment as compared to radiation therapy alone for adenocarcinoma of the stomach, pancreas, and large bowel. The Pt+CY+FU combinations proved to be uniquely efficaceous against advanced L1210 leukemia and specially in combination chemotherapy. CY was utilized at an optimum 50 mg/kg of body weight (range 25-75 mg/kg) preferably given at Day 3 in the 10-day testing. 5-FU was utilized at 75 mg/kg of body weight (range 50-100 mg/kg) at Day 3. HU was used in a high dosage of at least 1000 mg/kg of body weight (range 1000-1500 mg/kg). The 5-FU and the HU were utilized as ternary compositions only with cyclophosphamide and the platinum compound.

HIGH-DOSE HYDROXYUREA USED WITH CYCLOPHOSPHAMIDE AND PT NSC 271674 (Pt-307)

Hydroxyurea is utilized in combination therapy at a high dosage of at least 1000 mg/kg of body weight (range 1000-1500 mg/kg). At this dosage when used alone it is only minimally effective. In triple drug regimen involving Pt+Cy and the hydroxyurea (HU), the cure rate is 11% with the dual combinations and is increased to 53% upon inclusion of HU in the regimen. It is believed that HU may inhibit a process whereby potentially lethal DNA damage produced by PT+CY would otherwise be repaired.

EXAMPLE 1

Dichloro(1,2-diaminocyclohexane)platinum(II) (19.53 g; 0.052 mole) was suspended in 300 ml of water. Silver nitrate (15.20 g; 0.085 mole) was added and the mixture was stirred in a darkened flask overnight. The mixture was filtered and the filtrate was added to 9.90 grams of 4-carboxyphthalic acid (1,2,4-benzenetricarboxylic acid) (0.047 mole) dissolved in 200 ml of warm water. The reaction mixture was kept in a darkened flask at room temperature for two hours and then stored at 5° C. overnight. The off-white precipitate was collected, washed thoroughly with water and dried in vacuo over Drierite to yield 12.0 g (55%) of 4-carboxyphthalato(1,2-diaminocyclohexane)platinum(II).

Elemental analyses (Galbraith Laboratories, Knoxville, Tennessee):

|    | % Calculated | % Found |
|----|--------------|---------|
| C  | 34.81        | 34.50   |
| H  | 3.48         | 3.85    |
| Pt | 37.70        | 37.08   |

The compound was insoluble in water but dissolved readily in 1% sodium bicarbonate solution with the evolution of carbon dioxide indicating the presence of a free carboxy group. It was also very soluble in dimethylsulfoxide (DMSO). It decomposed without melting at temperatures greater than 270° C.

Thin layer chromatography, with methanol as developer, of a DMSO solution (dissociation was suppressed) by the addition of 1,2,4-benzene-tricarboxylic acid to the solution) on an Eastman 13255 cellulose chromagram sheet gave an $R_F$ value of 0.75. Stannous chloride was the detecting agent.

The infrared spectrum of a KBr pellet gave absorbances at the following wavenumbers ($cm^{-1}$):
3450s, 3210s, 3100w, 2935s, 2860m, 2600w, 1720s, 1600s, 1490s, 1450m, 1350s, 1240m, 1160m, 1120m, 1090w, 1060s, 1028vw, 1025m, 980w, 915m, 860w, 840m, 800m, 760s, 700m, 670vw, 655w, 620m, 570vw, 510m, 440m, 360m, 305w.

EXAMPLE 2

Effective Dosage in Mice

The compound in 1% $NaHCO_3$ solution was tested against the L1210 leukemia in $BDF_1$ mice [$10^6$ cells given to mice on Day 0, treatment (ip) on Day 1 only] in laboratory and the following % increases in life span (%ILS) were noted:

| Dose, mg/kg | % ILS | |
|---|---|---|
| 5 | 70 | |
| 10 | 118 | |
| 20 | 119 | |
| 25 | 139 | |
| 40 | 232 | |
| 50 | 288 | (1 of 8 mice survived >60 days) |
| 60 | 174 | (1 of 8 mice survived >60 days) |

The compound singly and in combination regimen

When treatment was delayed until Day 3, 5 mg/kg gave 51% ILS, 42% ILS and 39% ILS in three experiments. In combination with cyclophosphamide (50 mg/kg) in Day 3 treatment, 5 mg/kg gave 416% ILS with 3 of 10>60 day survivors and 217% ILS with no >60 day survivors in two experiments. In combination with cyclophosphamide (50 mg/kg) and 5-fluorouracil (75 mg/kg) in Day 3 treatment, 5 mg/kg gave 673% ILS with 8 of 10>60 day survivors.

The approximate $LD_{50}$ was 75 mg/kg.

The compound was submitted to the Drug Development Branch of the National Cancer Institute and assigned NSC Number 271674. It was screened against the L1210 leukemia on a day 1, 5, 9 schedule and the following results were obtained:

| Dose, mg/kg | % ILS | Cures (of 10) |
|---|---|---|
| 25 | 344 | 5 |
| 12.5 | 191 | 2 |
| 6.25 | 163 | 1 |
| 3.13 | 46 | 0 |
| 1.56 | 33 | 0 |
| 0.78 | 27 | 0 |

A second screener obtained:

| Dose, mg/kg | % ILS | |
|---|---|---|
| 25 | 86 | |
| 12.5 | 147 | |
| 6.25 | 58 | (2 questionably toxic deaths were noted) |
| 3.13 | 41 | |
| 1.56 | 19 | |
| 0.78 | 19 | |

No cures were obtained by the second screener.

EXAMPLE 3

A Comparison of the In Vitro Activity of NSC-119875 and NSC-271674 Against an L1210 Leukemia with Acquired Resistance to NSC-119875* *Cis-dichlorodiamino platinum II

| Compound | $ID_{50}$ L1210 | ($\mu$g/ml) L1210/DDP |
|---|---|---|
| NSC-119875 (DDP) | 0.05 | 2.50 |
| NSC-271674 | 0.30 | 0.23 |

The $ID_{50}$ refers to the concentration of test compound required to inhibit the growth of either the L1210 or L1210/DDP (NSC-119875) resistant) cells by 50 percent.

A Comparison of the In Vivo Activity of NSC-119875 and NSC-271674 Against a P388 Leukemia with Acquired Resistance to NSC-119875

| | | P388 | | P388/DDP | |
|---|---|---|---|---|---|
| Compound | Dose (Mg/Kg) Days 1,5,9,13 | Survival (Days) | % ILS | Survival (Days) | % ILS |
| Control | — | 13.3 | | 11.0 | |
| NSC-119875 (DDP) | 6.7 | 32.6 | 145 | 15.5 | 41 |
| NSC-271674 | 20.0 | 20.7 | 56 | 33.3 | 201 |

P388/DDP refers to a tumor line with acquired resistance to NSC-119875. Data are expressed as survival in days and as a percentage increase in life span (% ILS).

A Comparison of the Activity of NSC-119875 and NSC-271674 Against a Panel of Mouse Tumors

| | | NSC-119875 | | | NSC-271674 | | |
|---|---|---|---|---|---|---|---|
| Tumor (Site, Parameter) | Schedule (ip) | Dose Range (mg/kg/inj) | Optimal Dose (mg/kg/inj) | % T/C | Dose Range (mg/kg/inj) | Optimal Dose (mg/kg/inj) | % T/C |
| B16 melanoma ip, ST* | D1-9 | 16-0.5 | 2 | 193 | 25-0.39 | 6.25 | 171 |
| ip, ST* | D1-9 | 16-0.5 | 1 | 166 | 12.5-0.39 | 1.56 | 159 |
| L1210 | D1-9 | 16-0.5 | 2 | 151 | 25-0.39 | 0.78 | 174 |
| ip, ST | D1-9 | 16-0.5 | 2 | 182 | 12.5-0.39 | 1.56 | 325 |
| Lewis lung | D1-9 | 16-0.5 | 2 | 135 | 25-0.39 | 3.12 | 122 |
| iv, ST | D1-9 | 16-0.5 | 2 | 177 | 12.5-0.39 | 6.25 | 127 |
| CD8F1 mammary | Q7DX5 | 16-0.5 | 8 | 0 | 25-0.39 | 6.25 | 11 |
| sc, TW** | Q7DX5 | 32-1.0 | 8 | 0 | 50-1.56 | 25 | 25 |
| Colon #38 | D2,9 | 16-0.5 | 8 | 42 | 25-0.39 | 12.5 | 50 |

| Tumor (Site, Parameter) | Schedule (ip) | NSC-119875 | | | NSC-271674 | | |
|---|---|---|---|---|---|---|---|
| | | Dose Range (mg/kg/inj) | Optimal Dose (mg/kg/inj) | % T/C | Dose Range (mg/kg/inj) | Optimal Dose (mg/kg/inj) | % T/C |
| sc, TW | D2,9 | 32–1.0 | 16 | 11 | 50–1.56 | 50 | 33 |

*Survival time (mean or median) assay
**Tumor weight inhibition assay.
Data are expressed as a percentage of the survival time in days or the tumor weights in mg of the treated mice divided by the corresponding values for the control mice. All testing was performed using both platinum compounds in the same experiment. The criteria for activity are as follows: confirmed activity (activity from two separate laboratories) of a % T/C of 150 or more for survival systems and 10% or less for tumor weight inhibition assays. Lower levels of activity such as a % T/C of 125 for survival systems and 42% for tumor weight inhibition assays are considered statistically significant.

EXAMPLE 4

Toxicity of NSC-241240, NSC-250427, NSC-256927 and NSC-271674 Compared to the Toxicity of NSC-119875 in the Renal Toxicity Screening Protocol

| Parameters Measured | NSC-119875 | NSC-241240 | NSC-250427 | NSC-256927 | NSC-271674 |
|---|---|---|---|---|---|
| Body Weight Loss | 3 | 1 | 2 | 2 | 3 |
| Hematology- | | | | | |
| Hematocrit | 3 | 4 | 3 | 4 | 3 |
| White Blood Cell | 3 | 3 | 3 | 3 | 3 |
| Clinical Chemistry- | | | | | |
| Blood Urea Nitrogen | 3 | 1 | 1 | 1 | 1 |
| Creatinine | 3 | 1 | 1 | 1 | 1 |
| Serum Glutamic Pyruvic Transaminase | 3 | 3 | 5 | 3 | 3 |
| Histopathology- | | | | | |
| Renal | 3 | 1 | 2 | 2 | 2 |
| Lymphatic | 3 | 1 | 2 | 4 | 1 |
| Hematopoietic | 3 | 5 | 4 | 4 | 5 |
| Gastrointestinal | 3 | 1 | 1 | 1 | 1 |
| TOTAL SCORE | 30 | 21 | 24 | 25 | 23 |

Scoring:
1 = much less severe than NSC-119875
2 = slightly less severe than NSC-119875
3 = as severe as NSC-119875
4 = slightly more severe than NSC-119875
5 = much more severe than NSC-119875
NSC-119875 - cis-dichlorodiamino platinum II
NSC-241240 - diamine[1,1-cyclobutanedicarboxylato (2-)-0,0']platinum
NSC-250427 - sulfato(1,2-diaminocyclohexane)platinum (II)
NSC-256927 - bis-isopropylamine-cis-dichloro-trans-dihydroxy platinum (IV)
NSC-271674 - 4-carboxyphthalato(1,2-diaminocyclohexane)platinum (II)

The present compound (NSC 271674) has shown superior results in testing for renal toxicity against the parent compound (NSC 119875, cis-dichlorodiamino platinum II) and further the present compound appears to be active against strains of murine leukemia wherein the same NSC 119875 has exhausted its activity.

We claim:

1. A method of alleviating L1210 murine leukemia which comprises administering 4-carboxyphthalato (1,2-diaminocyclohexane)platinum(II) or alkali metal salts thereof I.P. and at anti-murine leukemia dosage to a mouse of 5–60 mg/kg for up to 10 days.

2. The method of claim 1 wherein the dosage of 4-carboxyphthalato(1,2-diaminocyclohexane)platinum(II) and alkali metal salts thereof is 50 mg/kg of body weight.

3. The method of claim 1 wherein additionally an L1210 leukemia with acquired resistance to cis-dichlorodiamino platinum II is utilized.

4. A method of alleviating a murine tumor selected from one member of the group consisting of B16 melanoma, Lewis lung, CD8F1 mammary, and Colon #38 which comprises administering 4-carboxyphthalato(1,2-diamino-cyclohexane)-platinum(II) or alkali metal salts thereof at an anti-murine tumor dosage to a mouse of 5–60 mg/kg for up to 10 days.

* * * * *